(12) United States Patent
Bowman et al.

(10) Patent No.: US 9,770,251 B2
(45) Date of Patent: Sep. 26, 2017

(54) SHAPED REMOVAL DEVICE

(71) Applicant: MicroVention, Inc., Tustin, CA (US)

(72) Inventors: Heath Bowman, Trabuco Canyon, CA (US); Shawn O'Leary, San Juan Capistrano, CA (US)

(73) Assignee: MicroVention, Inc., Tustin, CA (US)

( * ) Notice: Subject to any disclaimer, the term of this patent is extended or adjusted under 35 U.S.C. 154(b) by 146 days.

(21) Appl. No.: 13/966,135

(22) Filed: Aug. 13, 2013

(65) Prior Publication Data

US 2014/0046359 A1 Feb. 13, 2014

Related U.S. Application Data

(60) Provisional application No. 61/682,592, filed on Aug. 13, 2012.

(51) Int. Cl.
*A61B 17/22* (2006.01)
*A61B 17/221* (2006.01)

(52) U.S. Cl.
CPC ...... *A61B 17/22032* (2013.01); *A61B 17/221* (2013.01); *A61B 2017/2212* (2013.01); *A61B 2017/22034* (2013.01)

(58) Field of Classification Search
CPC ...... A61F 2/013; A61F 2/01; A61F 2002/016; A61F 2230/0063; A61F 2230/0069; A61F 2230/0071; A61F 2250/0048; A61F 2002/018; A61F 2/86; A61F 2/89; A61F 2/90; A61F 2/91; A61F 2/915; A61F 2/07; A61F 2/2418; A61F 2002/011; A61F 2002/015; A61F 2002/91508; A61F 2002/91516; A61F 2002/91525; A61F 2002/91533; A61F 2002/9155; A61B 17/22032; A61B 17/221; A61B 17/22031; A61B 17/2212; A61B 17/22034; A61B 2017/2215; A61B 2017/2217; A61B 17/12168; A61B 17/12172; A61B 17/12177; A61B 17/12109; A61B 17/12113; A61B 17/12118
USPC .......... 606/127, 128, 200; 623/1.16
See application file for complete search history.

(56) References Cited

U.S. PATENT DOCUMENTS

| | | | |
|---|---|---|---|
| 5,395,390 A * | 3/1995 | Simon | A61F 2/90 606/198 |
| 6,663,650 B2 | 12/2003 | Sepetka et al. | |
| 6,824,545 B2 | 11/2004 | Sepetka et al. | |
| 7,875,050 B2 | 1/2011 | Samson et al. | |
| 8,100,935 B2 | 1/2012 | Rosenbluth et al. | |
| 8,252,017 B2 | 8/2012 | Paul, Jr. et al. | |
| 8,795,305 B2 | 8/2014 | Martin et al. | |
| 9,113,936 B2 * | 8/2015 | Palmer | A61B 17/221 |
| 2004/0199201 A1 * | 10/2004 | Kellett et al. | 606/200 |

(Continued)

OTHER PUBLICATIONS

WIPO, U.S. International Search Authority, International Search Report and Written Opinion mailed Nov. 8, 2013 in International Patent Application No. PCT/US2013/054785, 11 pages.

(Continued)

*Primary Examiner* — Darwin Erezo
*Assistant Examiner* — Katherine Schwiker
(74) *Attorney, Agent, or Firm* — Inskeep IP Group, Inc.

(57) ABSTRACT

An obstruction removal device is described having a variable external profile shape comprising one or more smaller profile regions and one or more larger profile regions.

4 Claims, 6 Drawing Sheets

(56) References Cited

U.S. PATENT DOCUMENTS

| | | |
|---|---|---|
| 2005/0216050 A1 | 9/2005 | Sepetka et al. |
| 2007/0038227 A1 | 2/2007 | Massicotte et al. |
| 2010/0087913 A1* | 4/2010 | Rabkin et al. ............... 623/1.16 |
| 2011/0009875 A1 | 1/2011 | Grandfield et al. |
| 2011/0106234 A1* | 5/2011 | Grandt ......................... 623/1.11 |
| 2012/0259402 A1 | 10/2012 | Grandt |
| 2012/0310251 A1 | 12/2012 | Sepetka et al. |
| 2013/0030461 A1 | 1/2013 | Marks et al. |
| 2013/0345739 A1* | 12/2013 | Brady et al. .................. 606/200 |
| 2014/0052162 A1* | 2/2014 | Cattaneo .............. A61B 17/221 |
| | | 606/159 |
| 2014/0243882 A1 | 8/2014 | Ma |
| 2014/0276403 A1 | 9/2014 | Follmer et al. |

OTHER PUBLICATIONS

WIPO, International Preliminary Examining Authority (U.S. Patent and Trademark Office), International Preliminary Report on Patentability mailed Feb. 26, 2015 in International Patent Application No. PCT/US2013/054785, 10 pages.

WIPO, U.S. International Search Authority, International Search Report and Written Opinion mailed Jul. 11, 2014 in International Patent Application No. PCT/US2014/025032, 8 pages.

* cited by examiner

US 9,770,251 B2

SHAPED REMOVAL DEVICE

RELATED APPLICATIONS

This application claims priority to U.S. Provisional Application Ser. No. 61/682,592 filed Aug. 13, 2012 entitled Shaped Removal Device, which is hereby incorporated herein by reference in its entirety.

BACKGROUND OF THE INVENTION

The present invention relates to devices used to capture and remove obstructions, such as clots or other matter, from the vascular system, and delivery of these devices to a target area within the vascular system.

The buildup of thrombus in vasculature can lead to formation of blood clots. The formation of clots can result in restricted blood supply to downstream areas of the vasculature. When these clots are located in the neurovascular system, these clots can lead to stroke. Recent technologies to deal with clot removal utilize devices designed to hold and capture the clot, followed by withdrawal of the device to physically remove these clots from the body. Several of these devices may fail to capture the clot in its entirety, or may promote clot fragmentation which may allow thrombus to dislodge and accumulate at another site, thus continuing the risk of stroke. In addition, several of these devices may promote endothelial denudation due to high friction between the device and the vessel wall. There is need for an obstruction removal device which reduces the likelihood of fragmented thrombus staying in the vasculature while maximizing the chance of mechanically capturing the clot, and limiting the risk of endothelial denudation.

SUMMARY OF THE INVENTION

In one embodiment according to the present invention, an obstruction removal device is described having a variable shape profile.

In one example of the previously described embodiment, the obstruction removal device has smaller profile and larger profile regions.

In one example of the previously described embodiment, the obstruction removal device has alternating smaller profile and larger profile regions.

In one example of the previously described embodiment, the obstruction removal device has substantially repetitive, alternating smaller profile and larger profile regions.

In one embodiment, the obstruction removal device is used to retrieve foreign body matter.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which.

DESCRIPTION OF EMBODIMENTS

Figure 1:
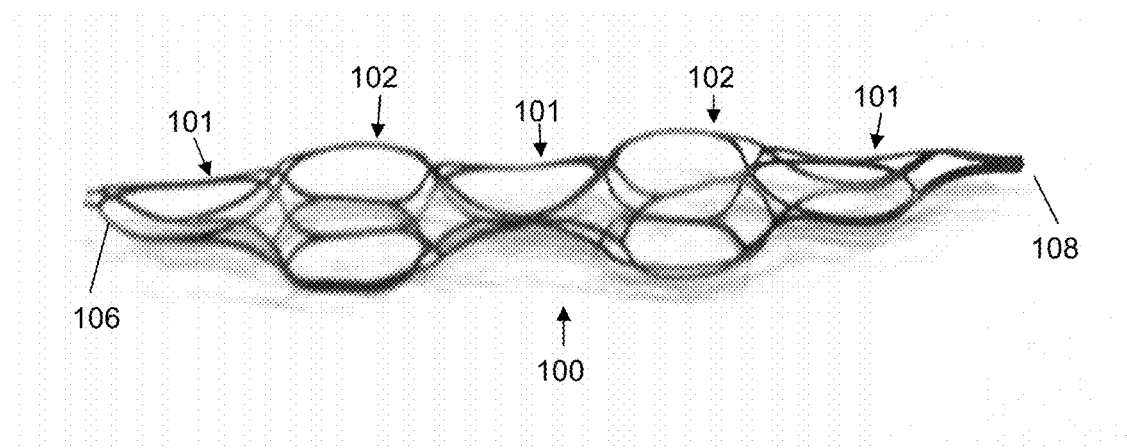
FIG. 1 is an obstruction removal device with a variable shape profile.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

For the purposes of the terminology described below, the terms clot, thrombus, embolus, and obstruction can be used synonymously. Though an obstruction removal device is described, the device can also be used to capture clot, thrombus, embolus, foreign bodies, or other matter.

FIG. 1 shows an obstruction removal device 100 in an expanded state with smaller profile regions 101 and larger profile regions 102. More specifically, the larger profile regions 102 may have a diameter, width, height, or any combination, which is larger than those of the smaller profile regions 101. Preferably, these regions 101, 102 are generally tubular in shape and composed of a plurality of open cells. In this particular figure, the smaller and larger profile regions alternate. The smaller and larger profile regions can alternate in a substantially repetitive pattern. Different examples of the same invention could employ various profile region configurations to provide the variable profile (i.e. a smaller profile region followed by a slightly larger profile section, followed by a still larger profile section; or other combinations). The device has a distal portion 108 and a proximal portion 106 which is connected to a pusher during the obstruction removal procedure.

Figure 2:
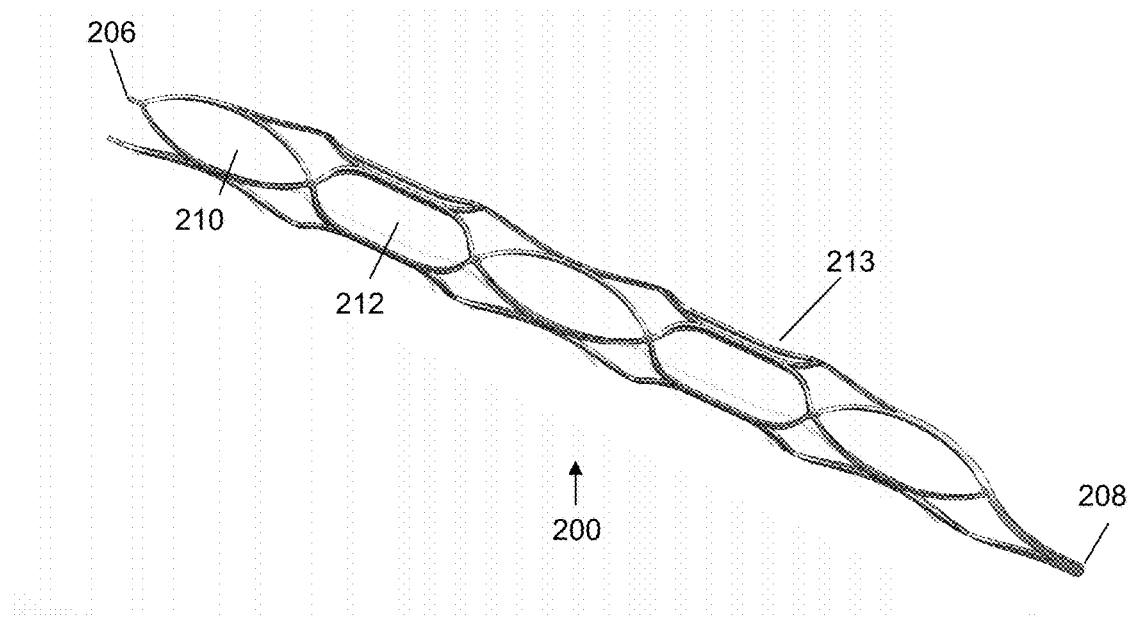
FIG. 2 is another example of an obstruction removal device with a variable shape profile.
Figure 3:
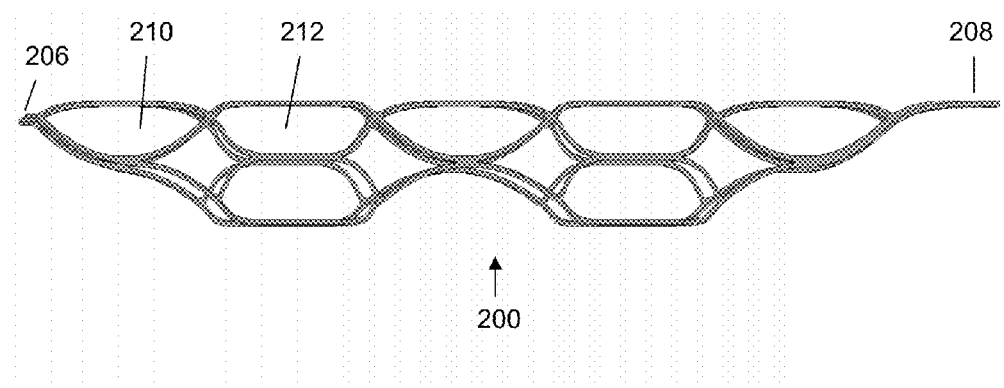
FIG. 3 is another view of the device shown in FIG. 2.

FIG. 2 shows another example of an obstruction removal device 200 in a cylindrical, expanded state, with a proximal portion 206 and a distal portion 208. FIG. 3 is another view of the device 200 shown in FIG. 2, where the orientation highlights the profile variation between regions.

The variable profile shape has many advantages over a more constant profile shape design. When deployed in a vessel the larger profile regions will be more likely to contact the blood vessel wall while the smaller profile regions will not. When typical clot removal or obstruction removal devices are deployed in a vessel, friction between the device and vessel wall can strip the surface of the vessel wall, leading to endothelial denudation. Because the larger profile regions are spaced apart, less of the device is in contact with the blood vessel at any given moment, thus reducing the likelihood of endothelial denudation occurring.

The variable shape can also aid in retrieving clots, obstructions, or foreign bodies. The larger profile regions of the device will contact the external portion of larger clots. The smaller profile regions—having a smaller cross sectional area—exert a higher radial force than the larger profile regions, thus exerting a greater retaining force on thrombus engaged by the smaller profile regions of the device. This results in better entrapment of the clot within the higher radial force location. The variable profile allows for better chance of clot engagement and retention by alternating larger profile regions, which are likely to engage outer clot portions, with the smaller profile regions which are useful for clot retention. Similarly, the inclusion of variable profile regions can prove versatile. For instance, the smaller profile regions may be useful for contacting and engaging smaller clots, or smaller portions of clots. Other designs utilizing a constant shape may have issues engaging smaller obstructions (if the retaining area of the device is significantly larger than said obstruction), or may have issues engaging larger obstructions (if the retaining area of the device is significantly smaller than said obstruction). Using a device which varies larger and smaller profile regions can prove versatile for a range of clot sizes.

The obstruction removal device may be made of nitinol, stainless steel, cobalt chromium, or other similar materials, or combinations of those or similar materials. The device may be fabricated from a solid sheet or a hypotube.

Figure 4:
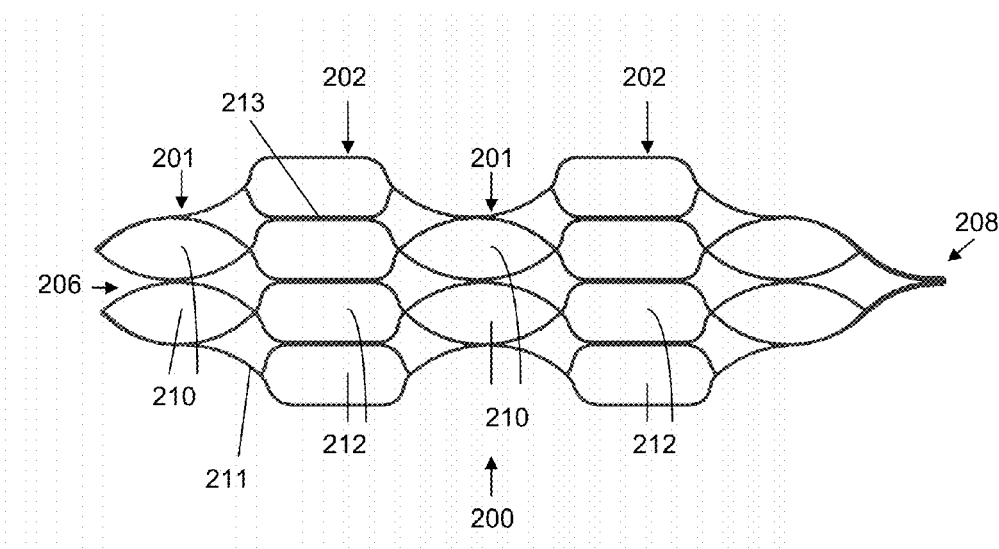
FIG. 4 is a sheet used to create the obstruction removal device of FIGS. 2 and 3.
Figure 5:
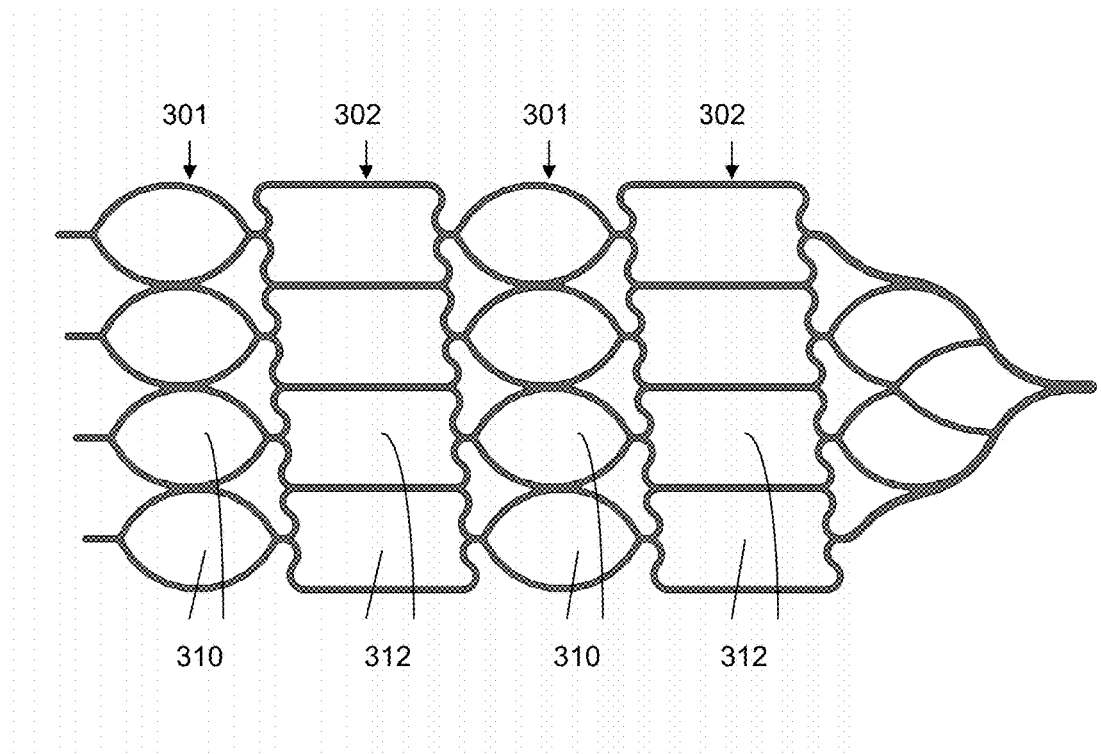
FIG. 5 is another example of a sheet used to create an obstruction removal device.

FIGS. 4 and 5 show design configurations used to create the obstruction retrieval device. In these design configurations the general profile of the obstruction removal device is laser-cut from a solid sheet of material (such as nitinol, stainless steel, cobalt chromium, or similar materials, or combinations thereof). The solid sheet may be a rolled flat plate. Other known cutting techniques can also be used to achieve the profile of the obstruction removal device. FIG. 4 shows a design configuration which has been cut to achieve smaller 201 and larger 202 profile regions. FIG. 5 shows a design configuration which has been laser cut to have a substantially constant external profile (no substantial external profile variation between regions 301 and 302).

Various shapes and/or patterns can be created through the laser-cutting operation in order to vary the sectional properties of the obstruction removal device. In FIG. 4, the smaller profile regions 201 have a particular cell pattern including two adjacent, oval or elliptical cells 210 located lateral to each other. The larger profile regions 202 have another cell pattern composed of four adjacent, rectangular cells 212, laterally aligned with each other. The cells 210 are preferably directly connected to adjacent cells 212 and/or via intermediate members 211, forming a device 200 with three smaller profile regions 201 and two larger profile regions 202. In other words, each region 201 or 202 are aligned to form bands or rings along the device 200. Preferably, the proximal end 208 includes members that merge together to form a single point or triangular end that can be connected to a pusher. The distal end 206 preferably terminates with cells 210, not a single point.

In one example, only the cells 212 of region 202 are coupled together to form a complete circle or closed tubular shape (i.e., each elongated side of each cell 212 is connected to the side of an adjacent cell 212), while the cells 210 of regions 201 are bent or curved in a generally "V" shape or open tubular shape, but not connected to each other at their free sides. In another embodiment, both regions 201 and 202 form closed tubular shapes.

In one specific example, the cells 210 and 212 have a length between about 0.2 inch to about 0.4 inch, and are formed from Nitinol having a width between about 0.004 inch to about 0.01 inch. In another specific example, the regions 201 and 202 can expand to a diameter between about 0.07 inch and about 4 inches.

Many of the figures show the cells of the stent having a great deal of open space due to much of the material being cut away, thus leaving a relatively thin strut profile. One advantage of such a configuration is that the stent will glide easier within the vasculature since less material is in contact with the vessel wall, due to the thinness of the stent struts. Coupled with the variable profile of the stent, only a small amount of the stent will contact the vessel wall at any given moment (only the relatively thin struts within the larger shaped regions). This limits friction and endothelial denudation, thus making trackability within the vasculature much easier than a) denser profile stents and b) stents with a more consistent outer profile where much of the stent is in contact with the vessel wall.

For example, in the embodiment of FIG. 4, the sides 213 of the cells 202 will provide most, if not all, of the contact with the interior of the vessel. Conversely, the smaller diameter or profile of the other surfaces, such as those forming cells 210 and connecting between cells 210 and 212, may reduce or even eliminate most contact with the interior of the vessel. Thus, the device 200 may have only four areas of contact in each region 202 and eight total on the entire device 200, and yet have a total of fourteen cells total on the device 200. However, it should be understood that this number of contact areas can be increased by adding additional cells 212 or regions 202, allowing any numbers of contact points, such as between about 2-10 contact points per region 202 and about 2-40 contact points per device 200.

Though many of the figures show a large laser-cut open region comprising the cells, less laser cutting throughout the stent, or less laser cutting in particular regions of the stent can be used to create a thicker or denser stent profile and limit the amount of open space in the cells. Such a configuration may be desirable for use in capturing thicker or denser thrombus, where one would want to maximize the contact area between the stent and thrombus.

In FIG. 5, though the external profile region shape (i.e., the diameter) is substantially constant through most of the design, different cell patterns 310, 312 are used in different regions of the design. For example, regions 301 include four elliptical cells 310, which are located adjacent to each other and connected to each other directly along their sides. Similarly, regions 302 include four rectangular cells 312 that are located adjacent to each other and share further share a common sidewall member with each adjacent cell 312. These different patterns can affect the clot retention strength of a particular region and/or the external force applied to the vessel wall, thus these patterns can customized for particular regions of the obstruction removal device. Though the patterns shown are substantially consistent within the particular profile region, different combinations of patterns in various regions of the device can be used, particularly as these patterns serve to customize the properties of the particular region of the device.

Figure 6:
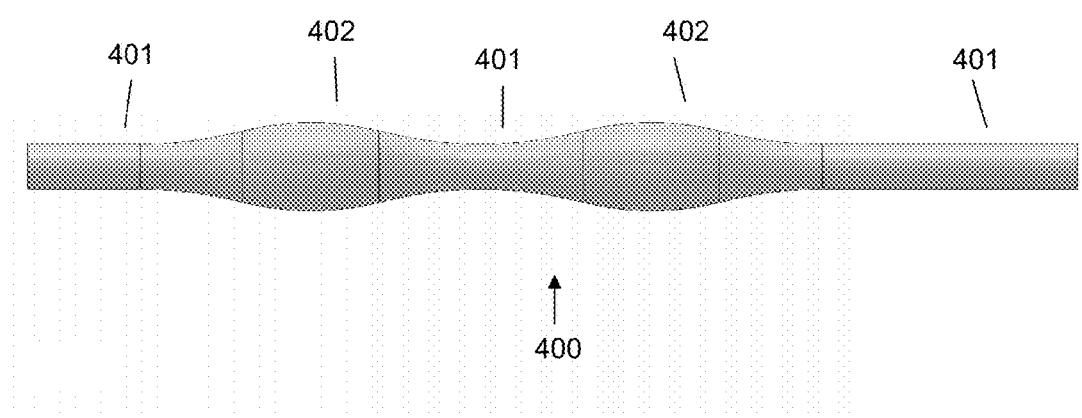
FIG. 6 is a mandrel used to help shape an obstruction removal device.

A mandrel 400 shown in FIG. 6, which may include smaller profile regions 401 and larger profile regions 402, is used as part of the shape configuring process. After laser-cutting, the plate is drawn over the mandrel and the ends of the plate and other connection points can be welded together to produce the cylindrical profile. Subsequent heat treatment over the mandrel will produce the final shape. Alternatively, after laser-cutting, the plate can be positioned over the cylindrical mandrel, heat treated, then the ends and other connection points can be welded together to produce the final shape. The different shaped regions 401, 402 on the mandrel help enhance the shaping of the corresponding region of the device which sits over that portion of the mandrel.

Figure 7:
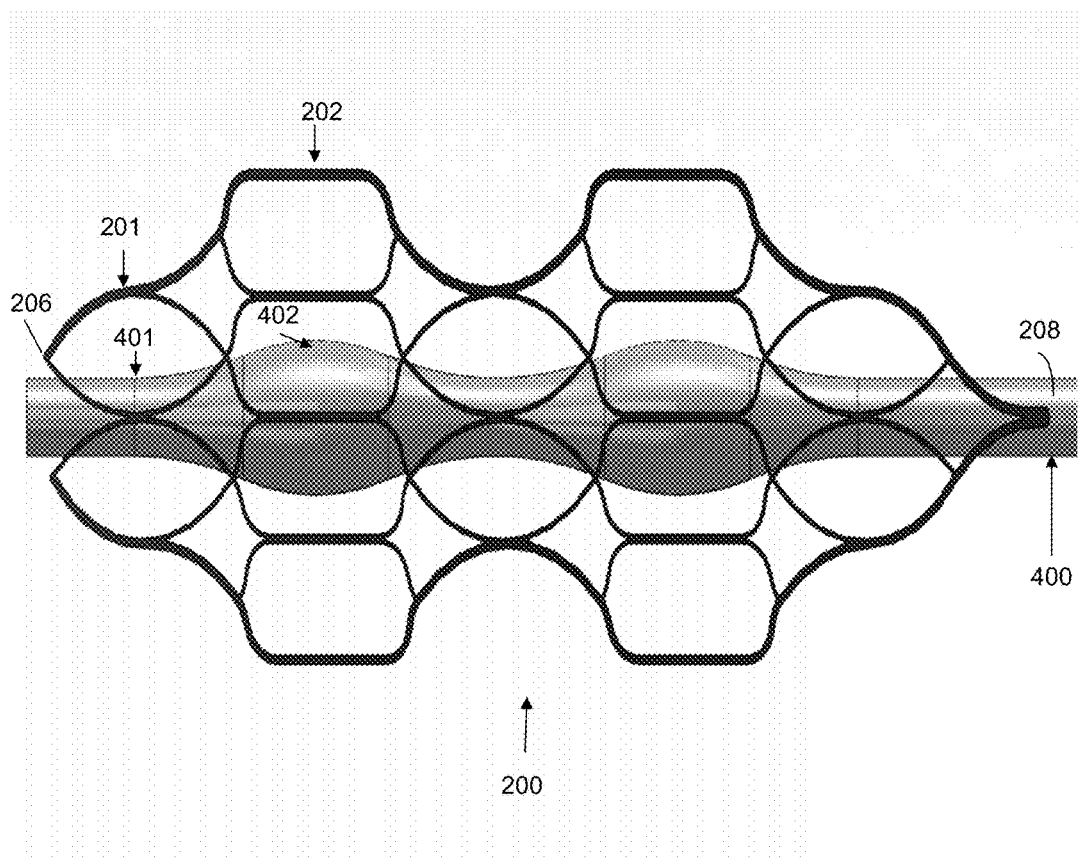
FIG. 7 is the sheet of FIG. 4 superimposed over the mandrel of FIG. 6 used to set the shape of the obstruction removal device of FIGS. 2 and 3.

FIG. 7 shows the plate design from FIG. 4 superimposed over the mandrel 400, as it would be placed over the mandrel prior to collapsing the plate physically over the mandrel. The smaller profile region of the device 201 corresponds to the smaller profile mandrel region 401 and the larger region 202 corresponds to the larger profile mandrel region 402 to help reinforce the shaping of the particular region of the device. Once placed over the mandrel, the device is heat treated to reinforce the shaping profile. After shaping and heat treating over the mandrel, and welding the connection points, the final product as shown in FIGS. 2 and 3 is achieved.

FIG. 5 shows a substantially constant profile shape design configuration. When this design is drawn and heat treated over the mandrel, the resulting obstruction removal device shape could still have a variable profile shape based on the shape of the mandrel. Using the mandrel with variable profile regions shown in FIG. 6 would result in a variable profile in regions 301, 302 of the design which correspond to regions 401, 402 of the mandrel. This profile variability will not be to the degree of the device made from the rolled flat plate shown in FIG. 4, which utilizes a variable shape profile in the plate itself. In this manner, the degree of variance in the outer diameter of particular regions can be controlled by the shape of the device design prior to placement on the mandrel, or by the shape of the mandrel used to help shape the obstruction removal device, or by both.

A hypotube can also be used to create the obstruction removal device profile. The hypotube may be made of nitinol, stainless steel, cobalt chromium, or other similar materials, or combinations of those or similar materials. It is then laser cut to create the various patterns and/or shapes within the device (i.e. cell shapes 210, 212 in FIGS. 2 and 3). The hypotube itself may have different profile shaped regions created during the formation of the hypotube, or may have a constant shape profile. After the hypotube is cut, it is placed on a mandrel and heat-treated to create its final shape. Similar to the procedure for the rolled plate shaping steps described above, a shaped mandrel may help reinforce the profile shape of particular segments of the hypotube, or may help form the profile shape of particular segments of the hypotube where no varied profile shape already exists.

An obstruction removal device of a substantially constant profile can be produced by creating a flat plate or hypotube design with a substantially constant profile shape, and shaping the device over a mandrel with a substantially constant profile shape.

The obstruction removal device may be self-collapsible/self-expandable, thus taking on a compressed form when sheathed inside a delivery device, and taking on its natural expanded form when freed from the sheath or delivery device.

Figure 8:
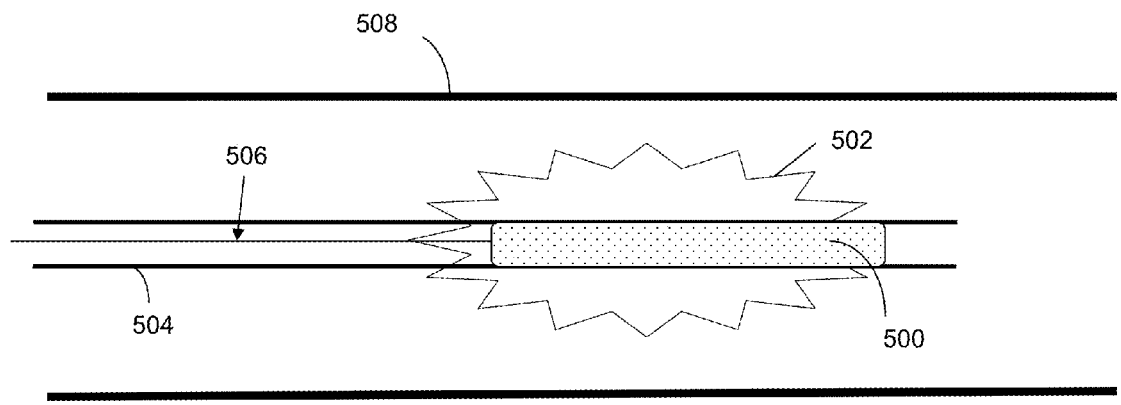
FIGS. 8-10 illustrate an example of a method of deploying the obstruction retrieval device.
Figure 9:
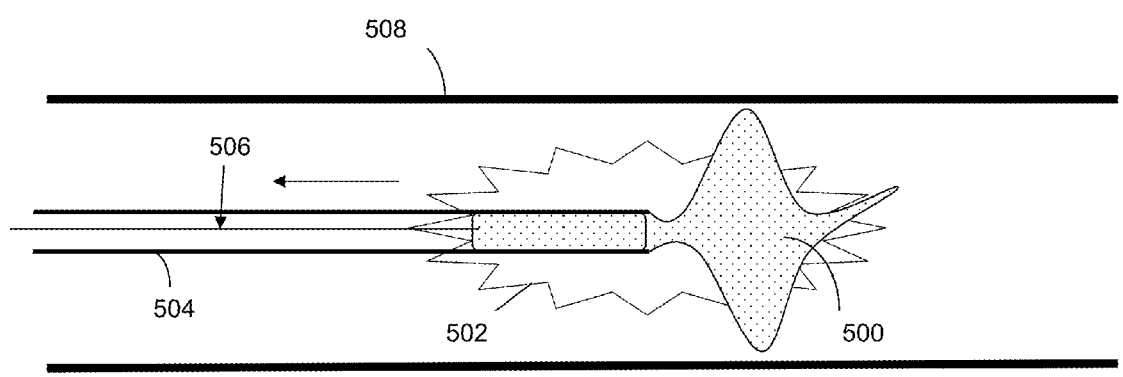
Figure 10:
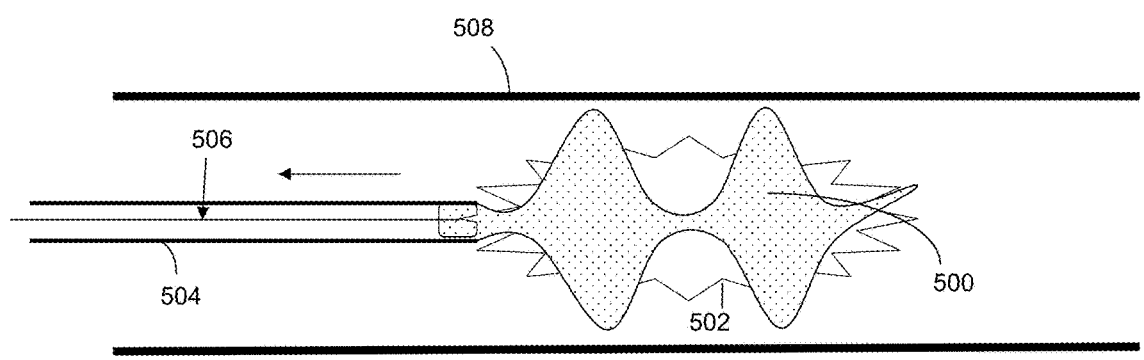

FIGS. 8-10 illustrate an example of a method of deploying the obstruction retrieval device in order to retrieve an obstruction. The proximal portion of the device may be connected to a deployment mechanism 506, such as a pusher. A guide catheter may be used to access the portion of the vasculature 508 where the clot or obstruction is located. A distal end of a microcatheter or delivery sheath 504 can be deployed to the region of the obstruction 502, which sheathes the obstruction removal device 500. The delivery sheath 504 can be retracted to expose and expand the obstruction removal device 500, or the obstruction removal device can be pushed from the delivery sheath to expand said device. Once the obstruction removal device grasps the obstruction, the device can be withdrawn from the region of the procedure, and the guide catheter can be withdrawn to remove the device from the vasculature. Alternatively, the device can be withdrawn into the guide catheter and removed as the guide catheter is withdrawn, or withdrawn through the guide catheter.

In one example, the proximal part of the obstruction removal device can include means to detach the obstruction removal device from the delivery mechanism, where the delivery mechanism connects to the proximal part of the device. The detachment means can include electrolytic, mechanical, thermal, or other means known in the art to induce severing and/or degradation of a linkage.

In an alternative embodiment, the obstruction removal device can be used to retrieve foreign objects, in addition to clots or other obstructions. Circumstances may arise where foreign objects, such as embolic coils normally used to fill an aneurysm, may break off or otherwise become detached within the vasculature. The device can be used to retrieve the foreign body utilizing a procedure similar to the procedure used during obstruction removal.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. An obstruction removal device consisting of:
    a first tubular region consisting of two adjacent elliptical cells;
    a second tubular region connected to said first tubular region and consisting of four rectangular cells;
    a third tubular region connected to said second tubular region and consisting of two adjacent elliptical cells;
    a fourth tubular region connected to said third tubular region and consisting of four rectangular cells;
    a fifth tubular region connected to said fourth tubular region and consisting of two adjacent elliptical cells,
    a plurality of connecting members connecting between each of said first tubular region, said second tubular region, said third tubular region, said fourth tubular region, and said fifth tubular region;
    wherein said first tubular region, said third tubular region, and said fifth tubular region have a first diameter, and said second tubular region and said fourth tubular region have a second diameter that is larger than said first diameter when said obstruction removal device is in an expanded state;
    wherein said two adjacent elliptical cells in each of said first tubular region, said third tubular region, and said fifth tubular region are laterally connected, have ends that are even with each other, are located symmetrically to each other relative to a longitudinal axis of said obstruction removal device, and are disconnected from each other along one of their lateral sides, forming an open tubular shape; and,
    wherein said four rectangular cells in each of said second tubular region and said forth tubular region have ends that are even with each other, are located symmetrically to each other relative to said longitudinal axis, are laterally adjacently connecting, and form a closed tubular shape.

2. The obstruction removal device of claim 1, wherein at least some of said plurality of connecting members merge to a single point and are connected to said fifth tubular region.

3. An obstruction removal device, consisting of:
a plurality of cells consisting of a first region, a second region, a third region, a fourth region, and a fifth region; and,
a plurality of connecting members connecting between each of said first region, said second region, said third region, said fourth region, and said fifth region;
wherein said first, third, and fifth regions expand to a first profile size and wherein said second and fourth regions expand to a second profile size, larger than said first profile size;
wherein said first region, said third region, and said fifth region each consist of two laterally connected elliptical cells that have ends even with each other, are located symmetrically to each other relative to a longitudinal axis of said obstruction removal device, and are disconnected from each other along one of their lateral sides, forming an open tubular shape; and,
wherein said second region and said fourth region each consist of four laterally adjacently connecting rectangular cells that have ends even with each other, are located symmetrically to each other relative to said longitudinal axis, and that form a closed tubular shape.

4. The obstruction removal device of claim 3, wherein said laterally adjacent elliptical cells in each of said first region, said third region, and said fifth region are each connected to each other laterally, forming a "V" shaped cross sectional shape.

* * * * *